United States Patent [19]

Selwitz et al.

[11] 4,262,145

[45] * Apr. 14, 1981

[54] NOVEL ETHERIFICATION PROCESS

[75] Inventors: Charles M. Selwitz, Monroeville; John G. McNulty, Glenshaw, both of Pa.

[73] Assignee: Gulf Research & Development Company, Pittsburgh, Pa.

[*] Notice: The portion of the term of this patent subsequent to Nov. 20, 1996, has been disclaimed.

[21] Appl. No.: 102,268

[22] Filed: Dec. 10, 1979

Related U.S. Application Data

[63] Continuation-in-part of Ser. No. 141, Jan. 2, 1979, abandoned, which is a continuation-in-part of Ser. No. 916,969, Jun. 19, 1978, Pat. No. 4,175,210.

[51] Int. Cl.$^3$ ............................................. C07C 41/06
[52] U.S. Cl. ................................ 568/689; 568/697; 568/579; 568/667
[58] Field of Search ............... 568/689, 697, 579, 667

[56] References Cited

U.S. PATENT DOCUMENTS

| | | | |
|---|---|---|---|
| 2,067,385 | 1/1937 | Evans et al. | 568/689 X |
| 3,135,807 | 6/1964 | Grasselli et al. | 568/697 X |
| 4,175,210 | 11/1979 | Selwitz et al. | 568/689 |

*Primary Examiner*—Howard T. Mars

[57] ABSTRACT

A process for converting an olefin, or a mixture of olefins, to an ether, or a mixture of ethers, which comprises reacting said olefin, or said mixture of olefins, with an alkanol in contact with silicatungstic acid.

23 Claims, No Drawings

NOVEL ETHERIFICATION PROCESS

This application is a continuation-in-part application of our Application Ser. No. 000,141, filed Jan. 2, 1979, now abandoned, entitled Novel Etherification Process, which in turn, was a continuation-in-part application of our Application Ser. No. 916,969, filed June 19, 1978, now U.S. Pat. No. 4,175,210, entitled Novel Etherification Process.

BACKGROUND OF THE INVENTION

1. Field of the Invention

This invention relates to a new and useful process for converting an olefin, or a mixture of olefins, to an ether, or a mixture of ethers, which comprises reacting said olefin, or said mixture of olefins, with an alkanol, or a mixture of alkanols, in contact with silicatungstic acid.

2. Description of the Prior Art

Present commercial methods for reacting an olefin with an alkanol to obtain an ether involve the use of a mineral acid catalyst, such as, for example, sulfuric acid. Unfortunately, such methods have a number of disadvantages. These can include, for example, severe corrosion, acid-handling difficulties, high loss of acid, and the costly step of reconcentrating a diluted acid. More significantly, these methods, being used primarily to convert branched olefins to ethers, do not readily convert a mixture of olefins and, in particular, the unbranched and cyclic olefins to ethers. Consequently, a need exists for a simple, economical process for converting all classes of olefins, or a mixture of olefins, to ethers. Accordingly, the present invention provides a process for converting an olefin, or a mixture of olefins, to an ether, or a mixture of ethers, which comprises reacting said olefin, or said mixture of olefins, with an alkanol in contact with silicatungstic acid.

SUMMARY OF THE INVENTION

We have discovered a novel process for converting a specific branched olefin, a specific diolefin or mixtures of said specific branched olefins and/or specific diolefins to an ether or a mixture of ethers which comprises reacting said olefin, or said mixture of olefins, with an alkanol, or a mixture of alcohols, in contact with silicatungstic acid.

DETAILED DESCRIPTION OF THE PROCESS

The branched olefins or diolefins that can be employed herein can be defined by the following structure:

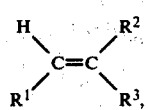

wherein $R^1$ is hydrogen, alkyl or alkenyl; but when $R^1$ is alkenyl $R^2$ and $R^3$ are hydrogen or alkyl; and when $R^1$ is hydrogen or alkyl, $R^2$ and $R^3$ are alkyls; said alkyls and alkenyls having from one to 12 carbon atoms, preferably from one to eight carbon atoms. Especially suitable branched olefins and diolefins that can be used will have from four to 14 carbon atoms, preferably from four to ten carbon atoms. Branched olefins suitable for use herein can include, for example, isobutylene, 2-methylpentene-2, 2-methylbutene-2 and 2,3-dimethyloctene-2. Diolefins suitable for use herein can include, for example, 1,3-pentadiene (piperylene) and 2-methylbutadiene (isoprene).

The alkanol that can be reacted with the branched olefins or diolefins defined above can be methanol, ethanol, isopropanol, normal propanol or mixtures thereof. In a preferred embodiment the alkanol is methanol.

The ethers produced as a result of the claimed reaction herein can be defined by the following structure:

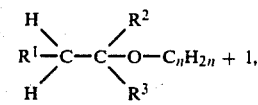

wherein $R^1$, $R^2$ and $R^3$ are as defined above and n is an integer from 1 to 3, preferably 1. Specific ethers that can be obtained from the claimed reaction include the following: 2-methoxy-2-methylbutane, methyl, t-butyl ether, ethyl t-butyl ether, isopropyl t-butyl ether, 2-methoxy-2-methyloctane, 2-methoxy-2,3-dimethyloctane, 3-methoxy-2,3-dimethyloctane, 3-methoxycyclopentene, 4-ethoxy-pentene-1, 4-propoxyl-pentene-1, 3-methyl-3-methoxy-butene-1, and methyl, sec-pentyl ether.

The alkanol can be mixed with the olefin in the present invention in any molar ratio. In general, the molar ratio of alkanol-to-olefin ranges from about 1:1 to about 15:1, preferably from about 2:1 to about 5:1.

The silicatungstic acid used as a catalyst herein is old and well-known and can be defined by the formula $SiO_2 \cdot 12WO_3$. A description of a typical preparation of silicatungstic acid is set forth, for example, in U.S. Pat. No. 3,361,518. The preparation of the deposition of silicatungstic acid on a silica is described, for example, in U.S. Pat. No. 2,982,799. In general, the weight percentage of silicatungstic acid relative to silica in the catalyst is about five to 100 percent, preferably about 30 to about 100 percent. The weight of catalyst per weight of reaction solution can be in the range of about 1:100 to about 1:1, preferably about 1:4 to about 1:40.

The present invention is carried out in batch form, that is, in a reactor with all the components therein. The temperature of the process of the present invention is not critical. In general, the temperature ranges from about 50° to about 200° C., preferably from about 80° to about 120° C. In the present invention the preferred pressure is atmospheric pressure (ambient pressure), but the pressure can range from about 0.1 to about 10 atmospheres, (9.646 to about 964.6 kPa) or even higher. The reaction time is also not critical and can be, for example, from about one minute to about 12 hours or even longer, but preferably from about one-half to about four hours.

In general, this product is a mixture of unreacted alcohol, unreacted olefin, the desired ether, and, depending on the alkanol used, dimethyl ether, diethyl ether or dipropyl ether. The liquid product is removed from the solid catalyst by filtration or by percolation. The desired ether is separated from the remaining product by any suitable procedure, but preferably by distillation at ambient pressure. Unreacted alcohol and olefin are recovered by distillation and can be recycled. The ether, or mixtures of ethers, obtained herein can be incorporated in gasoline to increase its octane rating.

DESCRIPTION OF PREFERRED EMBODIMENTS

The invention will be further described with reference to the experimental data.

The supported catalyst used in the experiments was prepared as follows:

Silicatungstic acid, purchased from Fisher Scientific, was dissolved in water to provide 422.9 grams of solution containing 21.82 percent $SiO_2.12WO_3$. The support was 215.3 grams of Davison silica gel, $SiO_2$, grade 70, 10–20 mesh which had been calcined at 538° C. for 10 hours. The support and solution were mixed to give 638.2 grams, net weight, of powder and this was dried at 121° C. for 24 hours to give 310 grams of dry product. This product was calcined at 400° C. for 16 hours to give the catalyst 30 percent silicatungstic acid on silica gel.

Several runs were carried out wherein a branched olefin or a diolefin and methanol were combined with 30 percent $SiO_2.12WO_3$ on silica (6.2 grams per 61.6 grams of solution) in a liquid phase batch reactor and agitated during the reaction period. The product obtained in each run was distilled to obtain the desired ether, which was analyzed by gas chromatography using a 10-foot 20 percent silicone (fluoro) QF-1 (FS-1265) column programmed from 50° to 195° C. The data obtained are summarized below in Table I.

We claim:

1. A process for converting an olefin, or mixture of olefins, to an ether, or a mixture of ethers, said olefin being a branched olefin or a diolefin defined by the following structure:

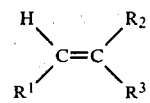

wherein $R^1$ is hydrogen, alkyl or alkenyl; but when $R^1$ is alkenyl $R^2$ and $R^3$ are hydrogen or alkyl; and when $R^1$ is hydrogen or alkyl, $R^2$ and $R^3$ are alkyls; said alkyls and alkenyls having from one to 12 carbon atoms, which comprises reacting in batch form in liquid phase said olefins, or mixtures of olefins, with an alkanol, or mixtures of alkanols, selected from the group consisting of methanol, ethanol, normal propanol and isopropanol, in a molar ratio of alkanol to olefin from about 1:1 to about 15:1, in contact with silicatungstic acid, with the weight of catalyst per weight of reaction solution being about 1:100 to about 1:1, at a temperature of about 50° to about 200° C. and a pressure of about 0.1 to about 10 atmospheres for about one minute to about 12 hours or even longer.

2. The process of claim 1 wherein said olefin has from four to 14 carbon atoms.

TABLE I

| Run No. | Olefin | Alcohol/Olefin Molar Ratio | Catalyst | Time, hr. | Temperature, °C. | Pressure, kPa (psig) | Product Analysis, Weight Per Cent | | | | Mol Per Cent Conversion to Ether |
|---|---|---|---|---|---|---|---|---|---|---|---|
| | | | | | | | $CH_3OCH_3$ | Unreacted $CH_3OCH_3$ | Unreacted Olefin | Ether | |
| 1 | 2-methyl-butene-2 | 2.5 | 30% $SiO_2$ . $12WO_3$ (6.2 grams per 61.6 grams of solution) | 1.0 | 113 | 275.6(40) | 1.2 | 54.5 | 18.2 | 26.1* | 50 |
| 2 | 1,3-pentadiene | 3.2 | unsupported $SiO_2$ . $12WO_3$ . $26H_2O$ (12.3 grams per 66 grams of solution) | 1.0 | 85–92 | 275.6(40) | 2.7 | 69.9 | 16.7 | 6.9** | 22 |
| 3 | 1,3-pentadiene | 3.2 | unsupported $SiO_2$ . $12WO_3$ . $26H_2O$ (6.0 grams per 60 grams of solution) | 1.0 | 67–71 | 275.6(40) | 1.1 | 67 | 25 | 3.0** | 8 |
| | | | | 1.0 | 90–93 | 275.6(40) | 1.7 | 65.3 | 5.1 | 8.5** | 23 |

*2-methoxy-2-methylbutane
**methyl sec-pentenyl ether

Referring to Table I, Run No. 1 shows that a branched olefin having a double bond and reacted with supported silicatungstic acid had a mol percent conversion of 50. Run No. 2 shows that a diolefin, 1,3-pentadiene, with pure, unsupported silicatungstic acid and an alcohol to olefin molar ratio of 3.2 had an acceptable mol percent conversion of 22. Run No. 3 shows that using a diolefin, 1,3-pentadiene, with silicatungstic acid in a batch system that there was a 8 mol percent conversion after 1 hour at 67°–71° C., but heating an additional hour at 90°–93° C. brought the conversion level to 23 mol percent.

Obviously, many modifications and variations of the invention, as hereinabove set forth, can be made without departing from the spirit and scope thereof, and therefore only such limitations should be imposed as are indicated in the appended claims.

3. The process of claim 1 wherein said olefin has from four to 10 carbon atoms.

4. The process of claim 1 wherein said alkyls and said alkenyls have from one to eight carbon atoms.

5. The process of claim 1 wherein $R^1$ is hydrogen.

6. The process of claim 1 wherein $R^1$ is an alkyl.

7. The process of claim 1 wherein $R^1$ is an alkenyl.

8. The process of claim 1 wherein $R^2$ and $R^3$ are hydrogen.

9. The process of claim 1 wherein $R^2$ and $R^3$ are alkyls.

10. The process of claim 1 wherein said olefin is a branched olefin.

11. The process of claim 1 wherein said olefin is a diolefin.

12. The process of claim 1 wherein said alkanol is methanol.

13. The process of claim 1 wherein said alkanol is ethanol.

14. The process of claim 1 wherein said alkanol is normal propanol.

15. The process of claim 1 wherein said alkanol is isopropanol.

16. The process of claim 1 wherein the molar ratio of alkanol to olefin is from about 2:1 to about 5:1.

17. The process of claim 1 wherein the weight of catalyst per weight of reaction solution is about 1:4 to about 1:40.

18. The process of claim 1 wherein the reaction temperature is about 80° to about 120° C.

19. The process of claim 1 wherein the pressure is about atmospheric.

20. The process of claim 1 wherein the reaction time is about one-half to about four hours.

21. The process of claim 1 wherein said silicatungstic acid has the formula: $SiO_2.12WO_3$.

22. The process of claim 1 wherein said silicatungstic acid is deposited on silica in an acid to silica weight ratio of about five to about 100 percent.

23. The process of claim 1 wherein said silicatungstic acid is deposited on silica in an acid to silica weight ratio of about 30 to about 100 percent.

* * * * *